(12) United States Patent
Belanger et al.

(10) Patent No.: US 6,750,250 B1
(45) Date of Patent: Jun. 15, 2004

(54) 11,12-OXIDOARACHIDONIC ACID DERIVATIVES AND METHODS OF THEIR USE IN TREATING DRY EYE DISORDERS

(75) Inventors: David B. Belanger, Cambridge, MA (US); Peter G. Klimko, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 66 days.

(21) Appl. No.: 10/170,426

(22) Filed: Jun. 12, 2002

Related U.S. Application Data

(60) Provisional application No. 60/304,988, filed on Jul. 12, 2001.

(51) Int. Cl.$^7$ .................. A61K 31/336; C07D 303/12; C07D 303/14; C07D 303/18; C07D 303/23
(52) U.S. Cl. ................ 514/475; 549/561; 549/563
(58) Field of Search .................. 514/475; 549/561, 549/563

(56) References Cited

U.S. PATENT DOCUMENTS

| | | | |
|---|---|---|---|
| 3,991,759 A | 11/1976 | Urquhart | 128/260 |
| 4,131,651 A | 12/1978 | Shah et al. | 424/78 |
| 4,370,325 A | 1/1983 | Packman | 424/245 |
| 4,409,205 A | 10/1983 | Shively | 424/78 |
| 4,744,980 A | 5/1988 | Holly | 424/78 |
| 4,804,539 A | 2/1989 | Guo et al. | 424/450 |
| 4,818,537 A | 4/1989 | Guo | 424/427 |
| 4,883,658 A | 11/1989 | Holly | 424/80 |
| 4,914,088 A | 4/1990 | Glonek et al. | 514/76 |
| 4,966,773 A | 10/1990 | Gressel et al. | 424/489 |
| 5,041,434 A | 8/1991 | Lubkin | 514/182 |
| 5,075,104 A | 12/1991 | Gressel et al. | 424/78.04 |
| 5,174,988 A | 12/1992 | Mautone et al. | 424/45 |
| 5,278,151 A | 1/1994 | Korb et al. | 514/76 |
| 5,290,572 A | 3/1994 | MacKeen | 424/602 |
| 5,294,607 A | 3/1994 | Glonek et al. | 514/76 |
| 5,371,108 A | 12/1994 | Korb et al. | 514/762 |
| 5,403,841 A | 4/1995 | Lang et al. | 514/226.8 |
| 5,578,586 A | 11/1996 | Glonek et al. | 514/76 |
| 5,696,166 A | 12/1997 | Yanni et al. | 514/573 |
| 5,800,807 A | 9/1998 | Hu et al. | 424/78.04 |
| 6,153,607 A | 11/2000 | Pflugfelder et al. | 514/178 |

OTHER PUBLICATIONS

Gao et al., "Total Synthesis of (−)–Dactylynes," Heterocycles, vol. 42(2), pp. 745–774 (1996).

Han et al., —"A Short Catalytic Enantioselective Synthesis of the Vascular Antiinflammatory Eicosanoid (11R, 12S)–Oxidoarachidonic Acid," *Organic Letters*, vol. 2(22), pp. 3437–3438 (2000).

Katritzky et al., "Stereoselective Syntheses of β,γ–Unsaturated Esters and γ–Lactones: 1–(Benzotriazol–1–yl)–3–(diphenylphosphoryl)–1–ethoxy–1–propene, a Protected =$CCH_2CO_2Et$ Synthon Equivalent," *J. Org. Chem.*, vol. 62, pp. 4131–4136 (1997).

Lemp et al., "Report of the National Eye Institute/Industry Workshop on Clinical Trials in Dry Eyes," *The CLAO Journal*, vol. 21(4), pp. 221–231 (1995).

Marsh et al., "Topical Nonpreserved Methylprednisolone Therapy for Keratoconjuctivitis Sicca in Sjögren Syndrome," *Ophthalmology*, vol. 106(4), pp. 811–816 (1999).

McCulley et al., "Tear Film Structure and Dry Eye," *Contactologia*, vol. 20, pp. 145–149 (1998).

Ohno, M.; Otsuka, M. Organic Reactions, vol. 37, Chapter 1 (1989).

Sharpless et al., "The Osmium–Catalyzed Asymmetric Dihydroxylation: A New Ligand Class and a Process Improvement," *J. Org. Chem.*, vol. 57, pp. 2768–2771(1992).

Shine et al., Keratoconjunctivitis Sicca Associated with Meibomian Secretion Polar Lipid Abnormality, *Arch. Opthalmology*, vol. 116, pp. 849–852 (1998).

Zamboni et al., "The Stereospecific Synthesis of 14S, 15S–Oxido 5Z, 8Z, 10E, 12E–Eicosatetraenoic Acid," *Tetrahedron Letters*, vol. 24(45), pp. 4899–4902 (1983).

*Primary Examiner*—Ba K. Trinh
(74) *Attorney, Agent, or Firm*—Patrick M. Ryan

(57) ABSTRACT

11,12-Oxidoarachidonic acid derivatives and methods of their use for treating dry eye are disclosed.

12 Claims, No Drawings

11,12-OXIDOARACHIDONIC ACID DERIVATIVES AND METHODS OF THEIR USE IN TREATING DRY EYE DISORDERS

This application claims priority to U.S. Provisional Application, Serial No. 60/304,988, filed Jul. 12, 2001.

The present invention is directed to the treatment of dry eye disorders. In particular, the present invention is directed toward certain novel 11,12-oxidoarachidonic acid derivatives and their use in the treatment of dry eye.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, Report of the National Eye Institute/ Industry Workshop on Clinical Trials in Dry Eyes, *The CLAO Journal*, volume 21, number 4, pages 221–231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, Tear film structure and dry eye, *Contactologia*, volume 20(4), pages 145–49 (1998); and Shine and McCulley, Keratoconjunctivitis sicca associated with meibomian secretion polar lipid abnormality, *Archives of Ophthalmology*, volume 116(7), pages 849–52 (1998). Examples of phospholipid compositions for the treatment of dry eye are disclosed in U.S. Pat. Nos. 4,131,651 (Shah et al.), 4,370,325 (Packman), 4,409, 205 (Shively), 4,744,980 and 4,883,658 (Holly), 4,914,088 (Glonek), 5,075,104 (Gressel et al.), 5,278,151 (Korb et al.), 5,294,607 (Glonek et al.), 5,371,108 (Korb et al.) and 5,578,586 (Glonek et al.). U.S. Pat. No. 5,174,988 (Mautone et al.) discloses phospholipid drug delivery systems involving phospholipids, propellants and an active substance.

U.S. Pat. No. 3,991,759 (Urquhart) discloses the use of ocular inserts in the treatment of dry eye. Other semi-solid therapy has included the administration of carrageenans (U.S. Pat. No. 5,403,841, Lang) which gel upon contact with naturally occurring tear film.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Aside from the above efforts, which are directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye condition in post-menopausal women; U.S. Pat. No. 5,290, 572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

U.S. Pat. No. 5,696,166 (Yanni et al.) discloses compositions containing naturally occurring HETEs, or derivatives thereof, and their use in methods for treating dry eye. The compositions comprising HETEs increase ocular mucin secretion.

Recent studies have also claimed that known anti-inflammatory agents, such as methylprednisolone, provide relief of symptoms associated with dry eye. See, for example, Marsh, et al., Topical nonpreserved methylprednisolone therapy for keratoconjunctivitis sicca in Sjogren syndrome, *Ophthalmology*, Volume 106 (4), pages 811–816 (1999); and U.S. Pat. No. 6,153,607 (Pflugfelder et al.).

SUMMARY OF THE INVENTION

The present invention is directed to compounds, compositions and methods of use. The present invention is particularly directed to compositions and methods for the treatment of dry eye and other disorders requiring the wetting of the eye, including symptoms of dry eye associated with refractive surgery such as LASIK surgery. More specifically, the present invention discloses ophthalmic compositions containing 11,12-oxidoarachidonic acid derivatives, and methods using the same for treating dry eye type disorders. The compositions are preferably administered topically to the eye.

DETAILED DESCRIPTION OF THE INVENTION

The 11,12-oxidoarachidonic acid derivatives of the present invention are those of formula (I):

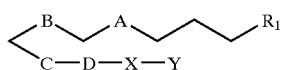

I wherein:

$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, wherein:

R is H or $CO_2R$ forms a pharmaceutically acceptable salt or a pharmaceutically acceptable ester;

$NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;

$OR^4$ comprises a free or functionally modified hydroxy group, e.g., $R^4$ is H, acyl; alkyl, cycloalkyl, aralkyl, or aryl;

Hal is F, Cl, Br, or I;

$SR^{20}$ comprises a free or functionally modified thiol group; and $R^{21}$ is H or $COSR^{21}$ forms a pharmaceutically acceptable salt or a pharmaceutically acceptable thioester;

A, B and D are the same or different and are $C_1$–$C_5$ alkyl, $C_2$–$C_5$ alkenyl, $C_2$–$C_5$ alkynyl, or a $C_3$–$C_5$ allenyl group;

C is an oxirane or cyclopropane;

X is $(CH_2)_m$ or $(CH_2)_mO$, wherein m is 1–6; and

Y is a phenyl ring optionally substituted with alkyl, halo, trihalomethyl, acyl, or a free or functionally modified hydroxy, amino, or thiol group; or X-Y is $(CH_2)_pY^1$; wherein p is 0–6; and

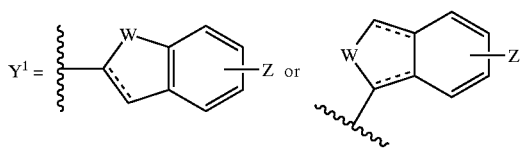

wherein:

W is $CH_2$, O, $S(O)_q$, $NR^8$, $CH_2CH_2$, CH=CH, $CH_2O$, $CH_2S(O)_q$, CH=N, or $CH_2NR^8$; wherein q is 0–2, and $R^8$ is H, alkyl, or acyl;

Z is H, alkyl, acyl, halo, trihalomethyl, or a free or functionally modified amino, thiol, or hydroxy group; and = is a single or double bond; or X-Y is cyclohexyl or n-$C_5H_{11}$.

All of the compounds of the present invention are believed to be novel with the exception of compound 1 which is a naturally occurring substance that is commercially available from Cayman Chemical Co., Ann Arbor, Mich., or can be synthesized by the method of Corey et. al. (Corey et. al., Org. Lett., 2:3437–3438 (2000)):

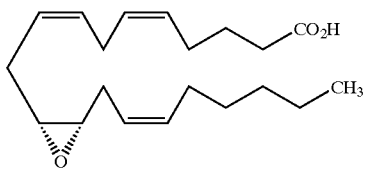

1

Included within the scope of the present invention are the individual enantiomers of the compounds of the present invention, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (Asymmetric Synthesis; J. D. Morrison and J. W. Scott, Eds.; Academic Press Publishers: New York, 1983–1985, volumes 1–5; Principles of Asymmetric Synthesis; R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (A Practical Guide to Chiral Separations by HPLC; G. Subramanian, Ed.; VCH Publishers: New York, 1994; Chiral Separations by HPLC; A. M. Krstulovic, Ed.; Ellis Horwood Ltd. Publishers, 1989), or by enantioselectively hydrolysis of a carboxylic acid ester sample by an enzyme (Ohno, M.; Otsuka, M. Organic Reactions, volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

As used herein, the terms "pharmaceutically acceptable salt", "pharmaceutically acceptable ester" and pharmaceutically acceptable thioester" means any salt, ester or thioester, respectively, that would be suitable for therapeutic administration to a patient by any conventional means without significant deleterious health consequences; and "ophthalmically acceptable salt", "ophthalmically acceptable ester" and "ophthalmically acceptable thioester" means any pharmaceutically acceptable salt, ester or thioester, respectively, that would be suitable for ophthalmic application, i.e. non-toxic and non-irritating.

The term "free hydroxy group" means an OH. The term "functionally modified hydroxy group" means an OH which has been functionalized to form: an ether, in which an alkyl, aryl, cycloalkyl, heterocycloalkyl, alkenyl, cycloalkenyl, heterocycloalkenyl, alkynyl, or heteroaryl group is substituted for the hydrogen; an ester, in which an acyl group is substituted for the hydrogen; a carbamate, in which an aminocarbonyl group is substituted for the hydrogen; or a carbonate, in which an aryloxy-, heteroaryloxy-, alkoxy-, cycloalkoxy-, heterocycloalkoxy-, alkenytoxy-, cycloalkenyloxy-, heterocycloalkenyloxy-, or alkynyloxycarbonyl group is substituted for the hydrogen. Preferred moieties include OH, $OCH_2C(O)CH_3$, $OCH_2C(O)C_2H_5$, $OCH_3$, $OCH_2CH_3$, $OC(O)CH_3$, and $OC(O)C_2H_5$.

The term "free amino group" means an $NH_2$. The term "functionally modified amino group" means an $NH_2$ which has been functionalized to form: an aryloxy-, heteroaryloxy-, alkoxy-, cycloalkoxy-, heterocycloalkoxy-, alkenyl-, cycloalkenyl-, heterocycloalkenyl-, alkynyl-, or hydroxy-amino group, wherein the appropriate group is substituted for one of the hydrogens; an aryl-, heteroaryl-, alkyl-, cycloalkyl-, heterocycloalkyl-, alkenyl-, cycloalkenyl-, heterocycloalkenyl-, or alkynyl-amino group, wherein the appropriate group is substituted for one or both of the hydrogens; an amide, in which an acyl group is substituted for one of the hydrogens; a carbamate, in which an aryloxy-, heteroaryloxy-, alkoxy-, cycloalkoxy-, heterocycloalkoxy-, alkenyl-, cycloalkenyl-, heterocycloalkenyl-, or alkynyl-carbonyl group is substituted for one of the hydrogens; or a urea, in which an aminocarbonyl group is substituted for one of the hydrogens. Combinations of these substitution patterns, for example an $NH_2$ in which one of the hydrogens is replaced by an alkyl group and the other hydrogen is replaced by an alkoxycarbonyl group, also fall under the definition of a functionally modified amino group and are included within the scope of the present invention. Preferred moieties include $NH_2$, $NHCH_3$, $NHC_2H_5$, $N(CH_3)_2$, $NHC(O)CH_3$, NHOH, and $NH(OCH_3)$.

The term "free thiol group" means an SH. The term "functionally modified thiol group" means an SH which has been functionalized to form: a thioether, where an alkyl, aryl, cycloalkyl, heterocycloalkyl, alkenyl, cycloalkenyl, heterocycloalkenyl, alkynyl, or heteroaryl group is substituted for the hydrogen; or a thioester, in which an acyl group is substituted for the hydrogen. Preferred moieties include SH, $SC(O)CH_3$, $SCH_3$, $SC_2H_5$, $SCH_2C(O)C_2H_5$, and $SCH_2C(O)CH_3$.

The term "acyl" represents a group that is linked by a carbon atom that has a double bond to an oxygen atom and a single bond to another carbon atom.

The term "alkyl" includes straight or branched chain aliphatic hydrocarbon groups that are saturated and have 1 to 6 carbon atoms. The alkyl groups may be interrupted by one or more heteroatoms, such as oxygen, nitrogen, or sulfur, and may be substituted with other groups, such as halogen, hydroxyl, aryl, cycloalkyl, aryloxy, or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, aryl, aryloxy, alkoxy, or alkyl. Preferred cycloalkyl groups include cyclopropyl, cyclobutyl, cyclopentyl and cyclohexyl.

The term "heterocycloalkyl" refers to cycloalkyl rings that contain at least one heteroatori such as O, S, or N in the ring, and can be fused or isolated. The rings may be substituted with other groups, such as halogen, hydroxyl, aryl, aryloxy, alkoxy, or alkyl. Preferred heterocycloalkyl groups include pyrrolidinyl, tetrahydrofuranyl, piperazinyl, and tetrahydropyranyl.

The term "alkenyl" includes straight or branched chain hydrocarbon groups having 1 to 6 carbon atoms with at least one carbon-carbon double bond, the chain being optionally interrupted by one or more heteroatoms. The chain hydrogens may be substituted with other groups, such as halogen. Preferred straight or branched alkenyl groups include allyl, 1-butenyl, 1-methyl-2-propenyl and 4-pentenyl.

The term "cycloalkenyl" includes straight or branched chain, saturated or unsaturated aliphatic hydrocarbon groups which connect to form one or more non-aromatic rings containing a carbon-carbon double bond, which can be fused or isolated. The rings may be substituted with other groups, such as halogen, hydroxyl, alkoxy, or alkyl. Preferred cycloalkenyl groups include cyclopentenyl and cyclohexenyl.

The term "heterocycloalkenyl" refers to cycloalkenyl rings which contain one or more heteroatoms such as O, N, or S in the ring, and can be fused or isolated. The rings may be substituted with other groups, such as halogen, hydroxyl, aryl, aryloxy, alkoxy, or alkyl. Preferred heterocycloalkenyl groups include pyrrolidinyl, dihydropyranyl, and dihydrofuranyl.

The term "carbonyl group" represents a carbon atom double bonded to an oxygen atom, wherein the carbon atom has two free valencies.

The term "aminocarbonyl" represents a free or functionally modified amino group bonded from its nitrogen atom to the carbon atom of a carbonyl group, the carbonyl group itself being bonded to another atom through its carbon atom.

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as alkyl, halogen, free or functonalized hydroxy, trihalomethyl, etc. Preferred aryl groups include phenyl, 3-(trifluoromethyl)phenyl, 3-chlorophenyl, and 4-fluorophenyl.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as alkyl or halogen. Examples of heteroaryl groups include imidazole, pyridine, indole, quinoline, furan, thiophene, pyrrole, tetrahydroquinoline, dihydrobenzofuran, and dihydrobenzindole.

The terms "aryloxy", "heteroaryloxy", "alkoxy", "cycloalkoxy", "heterocycloalkoxy", "alkenyloxy", "cydoalkenyloxy", "heterocycloalkenyloxy", and "alkynyloxy" represent an aryl, heteroaryl, alkyl, cycloalkyl, heterocycloalkyl, alkenyl, cycloalkenyl, heterocycloalkenyl, or alkynyl group, respectively, attached through an oxygen linkage.

The terms "alkoxycarbonyl", "aryloxycarbonyl", "heteroaryloxycarbonyl", "cycloalkoxycarbonyl", "heterocycloalkoxycarbonyl", "alkenyloxycarbonyl", "cycloalkenyloxycarbonyl", "heterocycloalkenyloxycarbonyl", and "alkynyloxycarbonyl" represent an alkoxy, aryloxy, heteroaryloxy, cycloalkoxy, heterocycloalkoxy, alkenyloxy, cycloalkenyloxy, heterocycloalkenyloxy, or alkynyloxy group, respectively, bonded from its oxygen atom to the carbon of a carbonyl group, the carbonyl group itself being bonded to another atom through its carbon atom.

Preferred compounds of the present invention include those of formula I, wherein:

$R^1$ is $CO_2R$, wherein R is H or $CO_2R$ forms a pharmaceutically acceptable salt or a pharmaceutically acceptable ester;

A and B are $C_{1-5}$ alkyl, alkenyl, or alkynyl or $C_{3-5}$ allenyl group;

C is

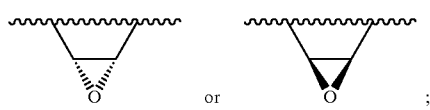

D is a $C_3$ alkyl, alkenyl, or alkynyl group;

X is $(CH_2)_m$ or $(CH_2)_mO$, wherein m is 1 or 2; and

Y is a phenyl ring optionally substituted with halo, trihalomethyl, or a free or functionally modified hydroxy group; or X-Y is $n-C_5H_{11}$ or cyclohexyl; or X-Y is $Y^1$; wherein

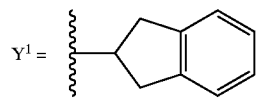

Among the particularly preferred compounds of formula I are compounds 1–4.

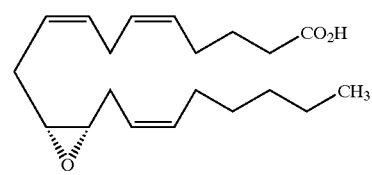

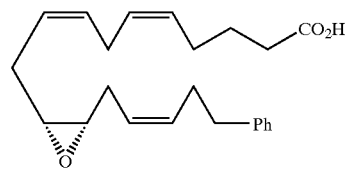

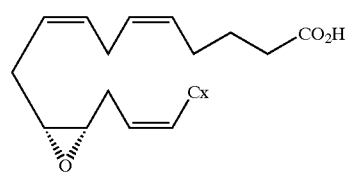

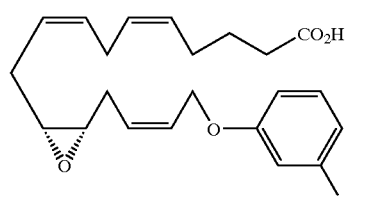

Compounds 2–4 can be synthesized as detailed in the following example 1–3:

EXAMPLE 1

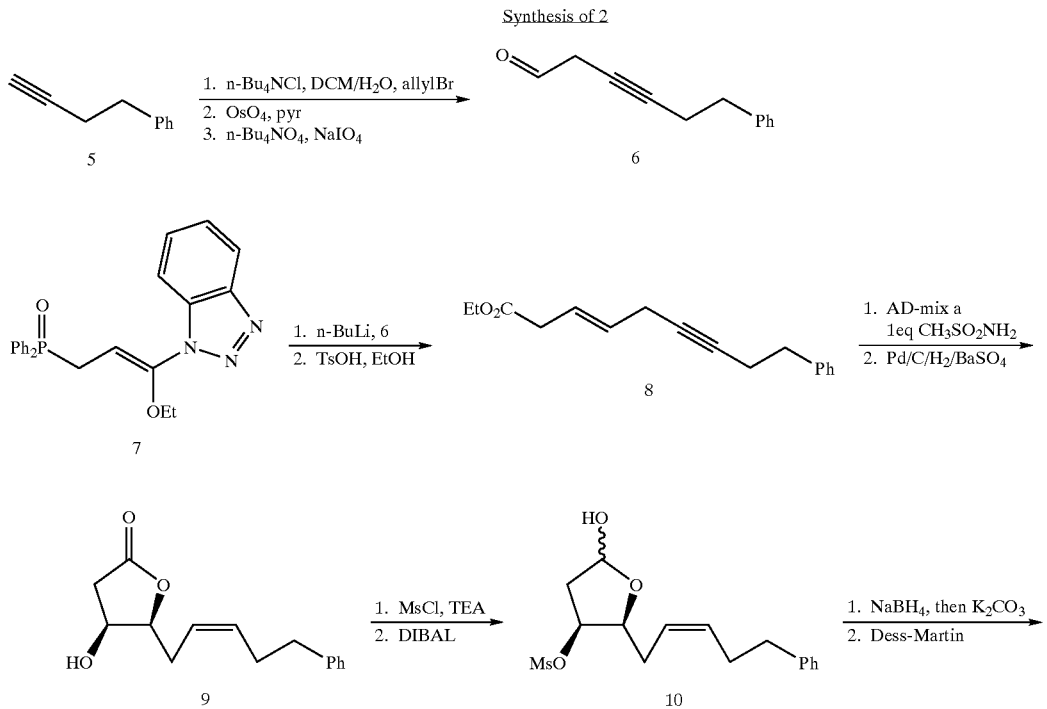

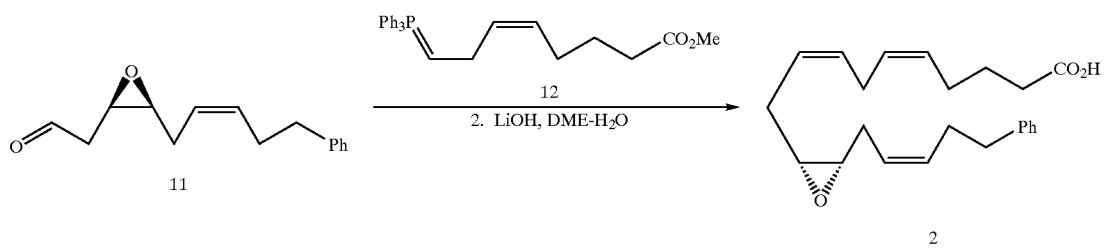

10-[(1R,2S)-2-(5-Phenyl-pent-2-en-1-yl)-oxiran-1-yl]-deca-5,8-dienoic acid (2)

Reaction of 4-phenyl-1-butyne (5; commercially available from Lancaster Synthesis, Windham, N.H.) with allyl bromide under phase-transfer conditions ($CH_2Cl_2$, n-$Bu_4NCl$, water, KOH), selective oxidation of the alkene moiety using catalytic $OsO_4$/pyr and stoichiometric N-methylmorpholine-N-oxide, and oxidative cleavage of the resultant diol using $NaIO_4$ affords 6-phenyl-hex-3-ynal (6). Lithiation of phosphine oxide 7 [Katritzky, Alan R., Feng, Daming, Lang, Hengyuan *J.Org.Chem.*, volume 62(12) page 4131 (1997)], Wittig condensation with 6, and heating of the intermediate dienyne (not shown) with p-toluenesulfonic acid in ethanol affords enyne 8. Asymmetric dihydroxylation of 8 with AD mix α (Aldrich Chemical Co., Milwaukee) and methanesulfonamide [Sharpless, K. B., Amberg, W., Bennani, Y. Crispino, G. A.; Hartung, J; Jeong, K. S.; Kwong, H.-L.; Morikawa, K.; Wang, Z.-M.; Xu, D. Zhang, X.-L. *J. Org. Chem.*, volume 57, page 2768 (1992)], followed by selective reduction with $H_2$ over Pd/$BaSO_4$, affords β-hydroxy lactone 9. Sequental treatment of 9 with $CH_3SO_2Cl/NEt_3$ and diisobutylaluminum hydride (DIBAL-H) provides lactol 10. Sodium borohydride reduction, $K_2CO_3$ treatment, and oxidation of the resulting β-hydroxyepoxide with the Dess-Martin reagent produces the epoxyaldehyde 11, Wittig olefination of 11 and known ylide 12 [Zamboni, R.; Milettee, S.; Rokach, J. *Tetrahedron Lett.*, volume 24, page 4899 (1983)] followed by saponification of the resulting methyl ester with LiOH in dimethoxyethane (DME)/water yields 2.

EXAMPLE 2

Synthesis of 3

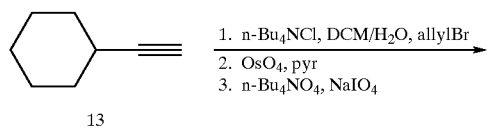

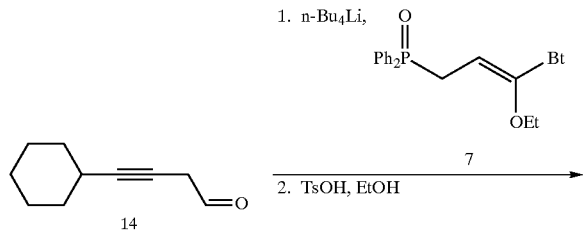

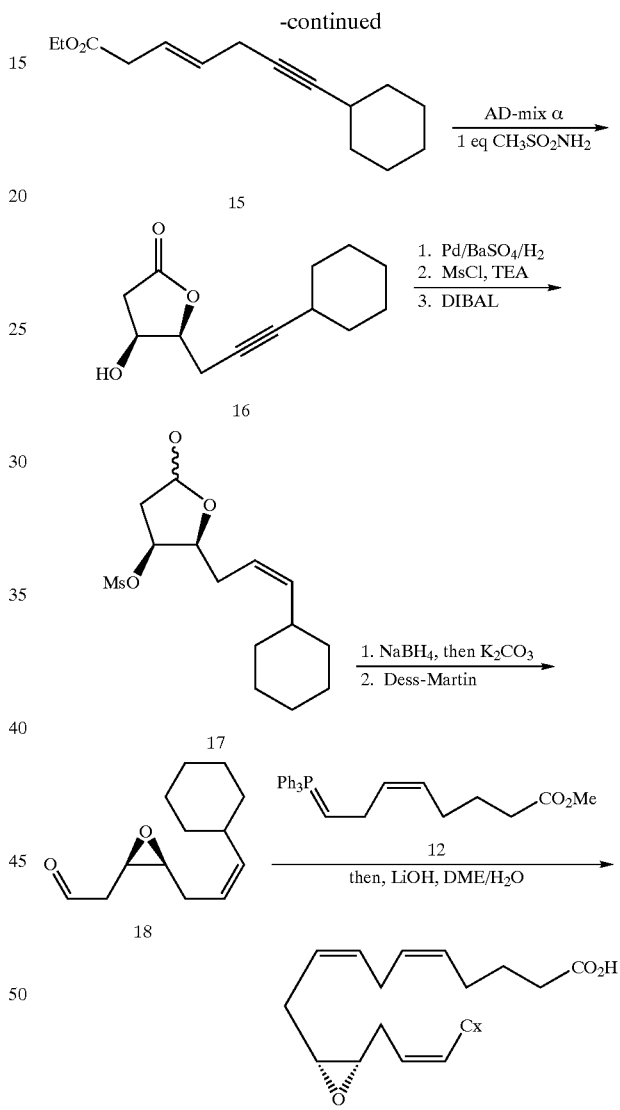

Synthesis of 10-[(1R,2S)-2-(3-Cyclohexylprop-2-enyl)-oxiran-1-yl]-deca-5,8-dienoic acid (3)

Allylation of cyclohexylacetylene (13; commercially available from Chemsampco Inc., Trenton, N.J., or preparable by the method of Wang and Fortunak, PCT Intl. Appl. WO 0018706 A1) with allyl bromide under phase-transfer conditions ($CH_2Cl_2$/water, KOH, allyl bromide, n-$BU_4NCl$) affords 4-cyclohexylbut-3-ynal (14), which is condensed with phosphine oxide 7 in the presence of n-BuLi to afford an intermediate dienyne (not shown). Heating the dienyne with p-toluenesulfonic acid in ethanol affords the desired enyne 15. Asymmetric dihydroxylation of 15 using AD mix α in the presence of $CH_3SO_2NH_2$ provides β-hydroxy lactone 16, which is sequentially reduced with $H_2$ over Pd/BaSO$_4$, treated with MsCl/NEt$_3$, and reduced with DIBAL-H to yield mesylate 17. Sodium borohydride reduction, $K_2CO_3$ treatment, and oxidation with the Dess-Martin reagent produces the epoxyaldehyde 18. Wittig olefination of 18 with ylide 12 followed by saponification with LiOH in DME/water affords 3.

EXAMPLE 3

Synthesis of 4

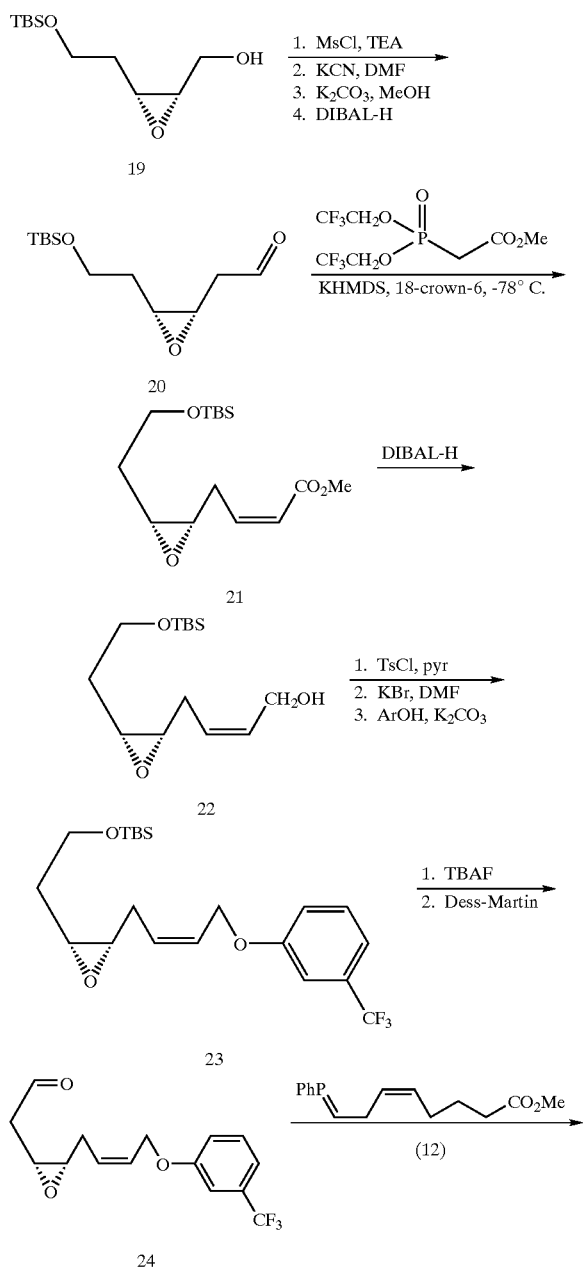

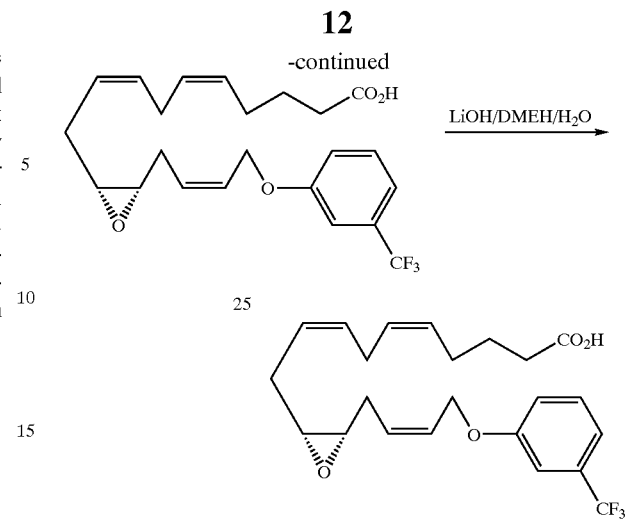

Synthesis of 10-[3-(3-Trifluoromethyl-phenoxymethyl)-oxiranyl]-deca-5,8-dienoic acid isopropyl ester (4)

Treatment of epoxide 21 [Gao, L.-X.; Murai, A. *Heterocycles*, volume 42(2), page 745 (1996)] sequentially with $CH_3SO_2Cl/NEt_3$, KCN in dimethylformamide, $K_2CO_3$ in methanol, and DIBAL-H affords aldehyde 20. Modified Horner-Emmons condensation of the aldehyde with $(CF_3CH_2O)_2P(O)CH_2CO_2Me$ in the presence of $KN(SiMe_3)_2$ and 18-crown-6 in THF at −78° C. affords cis-enoate 21. Reduction of 21 with DIBAL-H provides allyl alcohol 22, which is treated sequentially with p-toluenesulfonyl chloride/pyridine, KBr in dimethylformamide, and 3-trifluoromethylphenol/$K_2CO_3$ in acetone to give ether 23. Desilylation of 23 with tetra-n-butylammonium fluoride, followed by oxidation of the product alcohol with the Dess-Martin reagent, affords aldehyde 24. Wittig condensation of 24 with ylide 12 yields triene ester 25, which is saponified with LiOH in DME/water to afford 4.

Salt forms of the formula I compounds are preferred as it is believed that the neat salts are more stable than the corresponding neat acids. Preferred salts of the present invention are those wherein a terminal carboxylate of formula I (i.e., wherein $R^1$ is $CO_2R$) forms a salt with cations selected from: Na$^+$, K$^+$, NH$_4^+$, benzyltrimethylammonium ion, tetrabutylammonium ion, and phenyltrimethyl ammonium ion.

The compositions of the present invention comprise one or more compounds of formula I and a pharmaceutically acceptable carrier. The compositions are formulated in accordance with methods known in the art for the particular route of administration desired for the prevention, treatment or amelioration of the particular disease or disorder targeted. As used herein, the term "pharmaceutically acceptable carrier" refers to any formulation which is safe, and provides the appropriate delivery of an effective amount of one or more compounds of formula I for the prevention, treatment or amelioration of the disease or disorder targeted.

The compositions of the present invention comprise a pharmaceutically effective amount of one or more compounds of formula I. As used herein, a "pharmaceutically effective amount" is one which is sufficient to reduce or eliminate signs or symptoms of dry eye or other disorders requiring the wetting of the eye. Generally, the compounds of formula I will be contained in a composition of the present invention in a concentration range of about 0.00001 to 10 percent weight/volume ("% w/v"). Preferred topically administrable ophthalmic compositions will contain one or more compounds of formula I in a concentration of from about 0.00001–0.01% w/v.

The present invention is particularly directed to compositions useful in treating dry eye. Preferably, such compositions will be formulated as solutions, suspensions and other dosage forms for topical administration. Aqueous solutions are generally preferred, based on ease of formulation, biological compatibility (especially in view of the malady to be treated, e.g., dry eye-type diseases and disorders), as well as a patient's ability to easily administer such compositions by means of instilling one to two drops of the solutions in the affected eyes. However, the compositions may also be suspensions, viscous or semi-viscous gels, or other types of solid or semi-solid compositions. Suspensions may be preferred for compounds of formula (I) which are sparingly soluble in water.

Preferably, the compositions of the present invention will also contain a surfactant. Various surfactants useful in topical ophthalmic formulations may be employed. The surfactant(s) may provide additional chemical stabilization of the formula I compounds and may further provide for the physical stability of the compounds. In other words, the surfactants may aid in preventing chemical degradation of the compounds of formula I and also prevent the compounds from binding to the containers in which their compositions are packaged. As used herein, "an effective concentration of surfactant(s)" refers to a concentration that enhances the chemical and physical stability of formula I compound(s). Examples of surfactants include, but are not limited to: Cremophor® EL, polyoxyl 20 ceto stearyl ether, polyoxyl 40 hydrogenated castor oil, polyoxyl 23 lauryl ether and poloxamer 407 may be used in the compositions. A preferred surfactant is polyoxyl 40 stearate. The concentration of surfactant will vary, depending on the concentration of formula I compound(s) and optional ethanol present in the formulation. In general, however, the surfactant(s) concentration will be about 0.001 to 2.0% w/v. Preferred compositions of the present invention will contain about 0.1% w/v of polyoxyl 40 stearate.

The compositions of the present invention may also include various other ingredients, such as tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent concentration of about 0.1–1.5% w/v. Sodium chloride in the amount of 0.75% w/v is preferred.

An appropriate buffer system (e.g., sodium phosphate, sodium acetate, sodium cirate, sodium borate or boric acid) may be added to the compositions to prevent pH drift under storage conditions. The particular concentration will vary, depending on the agent employed. In general, however, such a concentration will range from about 0.02 to 2.0% w/v.

Antioxidants may be added to compositions of the present invention to protect the formula I compounds from oxidation during storage. Examples of such antioxidants include, but are not limited to, vitamin E and analogs thereof, ascorbic acid and derivatives, and butylated hydroxyanisole (BHA).

Compositions formulated for the treatment of dry eye-type diseases and disorders may also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous compositions which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of one or more compounds of formula I. Examples or artificial tears compositions useful as artificial tears carriers include, but are not limited to, commercial products, such as Tears Naturale®, Tears Naturale II®, Tears Naturale Free®, and Bion Tears® (Alcon Laboratories, Inc., Fort Worth, Tex.). Examples of phospholipid carrier formulations include those disclosed in U.S. Pat. Nos. 4,804,539 (Guo et al.), 4,883,658 (Holly), 4,914,088 (Glonek), 5,075,104 (Gressel et al.), 5,278,151 (Korb et al.), 5,294,607 (Glonek et al.), 5,371,108 (Korb et al.), 5,578,586 (Glonek et al.); the foregoing patents are incorporated herein by reference to the extent they disclose phospholipid compositions useful as phospholipid carriers of the present invention.

Other compounds designed to lubricate, "wet," approximate the consistency of endogenous tears, aid in natural tear build-up, or otherwise provide temporary relief of dry eye symptoms and conditions upon ocular administration the eye are known in the art. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises ("cps"). Preferred compositions containing artificial tears or phospholipid carriers will exhibit a viscosity of about 25 cps.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The preferred compositions of the present invention are intended for administration to a human patient suffering from dry eye or symptoms of dry eye. Preferably, such compositions will be administered topically. In general, the doses used for the above described purposes will vary, but will be in an effective amount to increase mucin production in the eye and thus eliminate or improve dry eye conditions. Generally, 1–2 drops of such compositions will be administered 1–10 times per day for the treatment of dry eye or other ocular disease or disorder. Preferably, 1–2 drops of the compositions will be administered 1–4 times per day.

A representative eye drop formulation is provided in Example 4 below.

EXAMPLE 4

| Ingredient | Amount (% w/v) |
| --- | --- |
| Compound of formula I | 0.00001–0.01 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.5 |
| Purified Water | q.s. 100% |

The above composition is prepared by the following method. The batch quantities of boric acid, sodium chloride, disodium edetate, and polyquaternium-1 are weighed and dissolved by stirring in 90% of the batch quantity of purified water. The pH is adjusted to 7.5±0.1 with NaOH and/or HCl. Under yellow light or reduced lighting, the batch quantity of the compound of formula I as a stock solution is measured and added. Purified water is added to q.s. to 100%. The mixture is stirred for five minutes to homogenize and then filtered through a sterilizing filter membrane into a sterile recipient.

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A compostion for the treatment of dry eye and other disorders requiring the wetting of the eye comprising a pharmaceutically acceptable carrier and a pharmaceutically effective amount of one or more compounds of the following formula I:

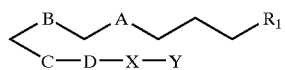

wherein:
  $R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, wherein:
    R is H or $CO_2R$ forms a pharmaceutically acceptable salt or a pharmaceutically acceptable ester;
    $NR^2R^3$ and $NR^5R^6$ are the same or different and comprise a free or functionally modified amino group, with the proviso that at most only one of $R^2$ and $R^3$ is OH or alkoxy and at most only one of $R^5$ and $R^6$ is OH or alkoxy;
  $OR^4$ comprises a free or functionally modified hydroxy group;
  Hal is F, Cl, Br, or I;
  $SR^{20}$ comprises a free or functionally modified thiol group; and
  $R^{21}$ is H or $COSR^{21}$ forms a pharmaceutically aceptable salt or a pharmaceutcally acceptable thioester;
A, B and D are the same or different and are $C_1$–$C_5$ alkyl, $C_2$–$C_5$ alkenyl, $C_2$–$C_5$ alkynyl, or a $C_3$–$C_5$ allenyl group;
C is an oxiran;
X is $(CH_2)_m$ or $(CH_2)_mO$, wherein m is 1–6; and
Y is a phenyl ring optionally substituted with alkyl, halo, trihalomethyl, acyl, or a free or functionally modified hydroxy, amino, or thiol group; or
X-Y is $(CH_2)_pY^1$; wherein p is 0–6; and

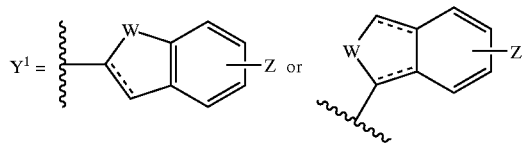

wherein:
  W is $CH_2$, O, $S(O)_q$, $NR^8$, $CH_2CH_2$, CH=CH, $CH_2O$, $CH_2S(O)_q$, CH=N, or $CH_2NR^8$; wherein q is 0–2, and $R^8$ is H, alkyl, or acyl;
  Z is H, alkyl, acyl, halo, trihalomethyl, or a free or functionally modified amino, thiol, or hydroxy group; and
  = is a single or double bond;
or X-Y is cyclohexyl or n-$C_8H_{11}$.

2. The composition of claim 1, wherein for the compound of formula I:
  $R^1$ is $CO_2R$, wherein R is H or $CO_2R$ forms a pharmaceutically acceptable salt or a pharmaceutically acceptable ester;
  A and B are $C_{1-5}$ alkyl, alkenyl, alkynyl or $C_{3-5}$ allenyl group;
  C is

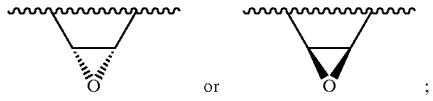

D is a $C_3$ alkyl, alkenyl, or alkynyl group;
  X is $(CH_2)_m$ or $(CH_2)_mO$, wherein m is 1 or 2; and
  Y is a phenyl ring optionally substituted with halo, trihalomethyl, or a free or functionally modified hydroxy group; or
  X-Y is n-$CH_5H_{11}$ or cyclohexyl; or
  X-Y is $Y^1$; wherein

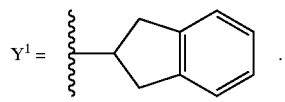

3. The composition of claim 2, wherein the compound of formula I is selected from the group consisting of:

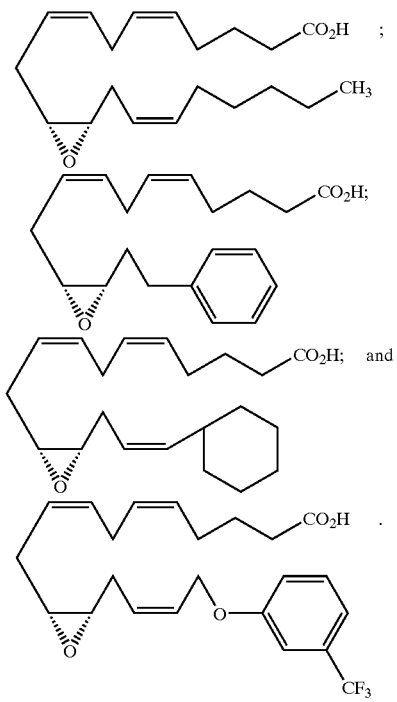

4. The composition of claim 1, wherein the composition is a topical ophthalmic formulation.

5. A method for the treatment of dry eye and other disorders requiring the wetting of the eye which comprises administering to a mammal a composition comprising a pharmaceutically acceptable carrier and a pharmaceutically effective amount of one or more compounds of the following formula I:

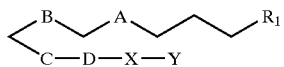
                                                I wherein:
$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, wherein:
  R is H or $CO_2R$ forms a pharmaceutically acceptable salt or a pharmaceutically acceptable ester;
  $NR^2R^3$ and $NR^5R^6$ are the same or different and comprise a free or functionally modified amino group, with the proviso that at most only one of $R^2$ and $R^3$ is OH or alkoxy and at most only one of $R^5$ and $R^6$ is OH or alkoxy;
  $OR^4$ comprises a free or functionally modified hydroxy group;
  Hal is F, Cl, Br, or I;
  $SR^{20}$ comprises a free or functionally modified thiol group; and
  $R^{21}$ is H or $COSR^{21}$ forms a pharmaceutically acceptable salt or a pharmaceutically acceptable thioester;
A, B and D are the same or different and are $C_1$–$C_5$ alkyl, $C_2$–$C_6$ alkenyl, $C_2$–$C_5$ alkynyl, or a $C_3$–$C_5$ allenyl group;
C is an oxirane;
X is $(CH_2)_m$ or $(CH_2)_mO$, wherein m is 1–6; and Y is a phenyl ring optionally substituted with alkyl, halo, trihalomethyl, acyl, or a free or functionally modified hydroxy, amino, or thiol group; or
X-Y is $(CH_2)_pY^1$; wherein p is 0–6; and

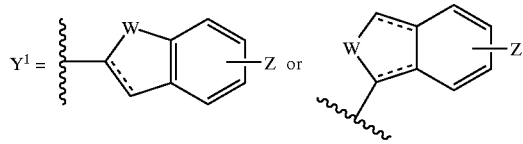

wherein:
W is $CH_2$, O, $S(O)_q$, $NR^8$, $CH_2CH_2$, CH=CH, $CH_2O$, $CH_2S(O)_q$, CH=N, or $CH_2NR^8$; wherein q is 0–2, and $R^8$ is H, alkyl, or acyl;
Z is H, alkyl, acyl, halo, trihalomethyl, or a free or functionally modified amino, thiol, or hydroxy group; and
= is a single or double bond;
or X-Y is cyclohexyl or n-$C_5H_{11}$.

6. The method of claim 5, wherein for the compound of formula I:
$R_1$ is $CO_2R$, wherein R is H or $CO_2R$ forms a pharmaceutically acceptable salt or a pharmaceutically acceptable ester;
A and B are $C_{1-5}$ alkyl, alkenyl, or alkynyl or $C_{3-5}$ allenyl group;
C is

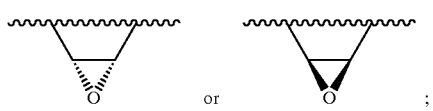

D is $C_3$ alkyl, alkenyl, or alkynyl group;
X is $(CH_2)_m$ or $(CH_2)_mO$, wherein m is 1 or 2; and
Y is a phenyl ring optionally substituted with halo, trihalomethyl, or a free or functionally modified hydroxy group; or
X-Y is n-$C_5H_{11}$ or cyclohexyl; or
X-Y is $Y^1$; wherein

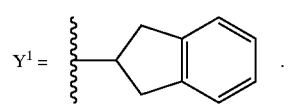

7. The method of claim 6, wherein the compound of formula I is selected from the group consisting of:

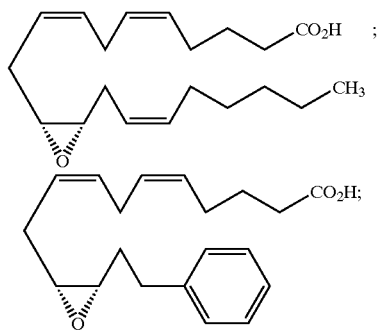

-continued

[structure: epoxide-containing fatty acid with CO₂H and cyclohexyl group]

and

[structure: epoxide-containing fatty acid with CO₂H and phenoxy-CF₃ group]

8. The method of claim 5, wherein the composition is a topical ophthalmic formulation.

9. The method of claim 5 wherein the dry eye and other disorders requiring the wetting of the eye is symptoms of dry eye associated with refractive surgery.

10. A compound of the following formula I:

$$\text{B-A-R}_1 \quad \text{C-D-X-Y} \quad \text{I}$$

wherein:
- $R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5tetrazol-1-yl, wherein:
  - R is H or $CO_2R$ forms a pharmaceutically acceptable salt or a pharmaceutically acceptable ester:
  - $NR^2R^3$ and $NR^5R^6$ are the same or different and comprise a free or functionally modified amino group, with the provision that at most only one of $R^2$ and $R^3$ is OH or alkoxy and at most only one of $R^5$ and $R^6$ is OH or alkoxy;
  - $OR^4$ comprises a free or functionally modified hydroxy group;
  - Hal is F, Cl, Br, or I;
  - $SR^{20}$ comprises a free or functionally modified thiol group; and
  - $R^{21}$ is H or $COSR^{21}$ forms a pharmaceutically acceptable salt or a pharmaceutically acceptable thioester;
- A, B and D are the same or different and are $C_1$–$C_5$ alkyl, $C_2$–$C_5$ alkenyl, $C_2$–$C_5$ alkynyl, or a $C_3$–$C_5$ allenyl group;
- C is an oxiran;
- X is $(CH_2)_m$ or $(CH_2)_mO$, wherein m is 1–6; and
- Y is a phenyl ring optionally substituted with alkyl, halo, trihalomethyl, acyl, or a free or functionally modified hydroxy, amino, or thiol group; or
- X-Y is $(CH_2)_pY^1$; wherein p is 0–6; and $Y^1 = $ [indole-Z structure] or [isoindole-Z structure]

wherein:

W is $CH_2$, O, $S(O)_q$, $NR^8$, $CH_2CH_2$, $CH=CH$, $CH_2O$, $CH_2S(O)_q$, $CH=N$, or $CH_2NR^8$; wherein q is 0–2 and $R^5$ is H, alkyl, or acyl;

Z is H, alkyl, acyl, halo, trihalomethyl, or a free or functionally modified amino, thiol, or hydroxy group; and = is a single or double bond;

or X-Y is cyclohexyl or n-$C_5H_{11}$, provided that the following compound is excluded:

[structure: epoxide fatty acid with CO₂H and CH₃]

11. The compound of claim 10, wherein for the compound of formula I:
- $R^1$ is $CO_2R$, wherein R is H or $CO_2R$ forms a pharmaceutically acceptable salt or a pharmaceutically acceptable ester;
- A and B are $C_{1-5}$ alkyl, alkenyl, or alkynyl or $C_{3-6}$ allenyl group;
- C is

[two epoxide structures shown] or ;

- D is a $C_3$ alkyl, alkenyl, or alkynyl group;
- X is $(CH_2)_m$ or $(CH_2)_mO$, wherein m is 1 or 2; and
- Y is a phenyl ring optionally substituted with halo, trihalomethyl, or a free or functionally modified hydroxy group; or
- X-Y is n-$C_5H_{11}$ or cyclohexyl; or
- X-Y is $Y^1$; wherein $Y^1 = $ [indane structure] .

12. The compound of claim 11, wherein the compound of formula I is selected group consisting of:

[structure: epoxide fatty acid with CO₂H and phenyl];

-continued
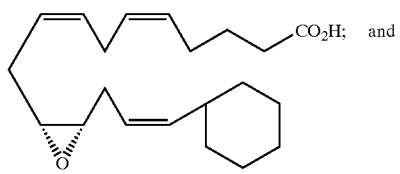 and
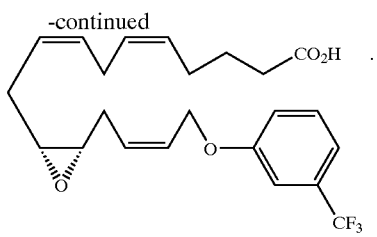
* * * * *

UNITED STATES PATENT AND TRADEMARK OFFICE
CERTIFICATE OF CORRECTION

PATENT NO. : 6,750,250 B1
DATED : June 15, 2004
INVENTOR(S) : Belanger et al.

It is certified that error appears in the above-identified patent and that said Letters Patent is hereby corrected as shown below:

Column 12,
Line 2, structure 25, the "$CO_2H$" should read -- $CO_2Me$ --.
Line 26, "Treatment of epoxide 21..." should read -- Treatment of epoxide 19 --.

Column 16,
Line 14, "Oxiran" should read -- Oxirane --.

Column 19,
Line 53, "Oxiran" should read -- Oxirane --.

Signed and Sealed this

Thirteenth Day of September, 2005

JON W. DUDAS
*Director of the United States Patent and Trademark Office*